(12) United States Patent
Journey et al.

(10) Patent No.: US 10,390,856 B2
(45) Date of Patent: Aug. 27, 2019

(54) SURGICAL IMPLANTATION INSTRUMENT

(75) Inventors: Michelle Journey, Carlsbad, CA (US); Sean Caffey, Manhattan Beach, CA (US); Mark Humayun, Glendale, CA (US); John Huculak, Mission Viejo, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 308 days.

(21) Appl. No.: 13/351,836

(22) Filed: Jan. 17, 2012

(65) Prior Publication Data
US 2013/0018412 A1 Jan. 17, 2013

Related U.S. Application Data

(60) Provisional application No. 61/433,832, filed on Jan. 18, 2011.

(51) Int. Cl.
| | | |
|---|---|---|
| A61B 17/28 | (2006.01) | |
| A61B 17/30 | (2006.01) | |
| A61B 17/00 | (2006.01) | |
| A61B 17/29 | (2006.01) | |
| A61F 9/00 | (2006.01) | |
| A61F 13/51 | (2006.01) | |

(52) U.S. Cl.
CPC ............ *A61B 17/30* (2013.01); *A61B 17/282* (2013.01); *A61B 2017/00858* (2013.01); *A61B 2017/00893* (2013.01); *A61B 2017/00995* (2013.01); *A61B 2017/2845* (2013.01); *A61B 2017/2945* (2013.01); *A61B 2017/2946* (2013.01); *A61F 9/0008* (2013.01); *A61F 2013/51071* (2013.01)

(58) Field of Classification Search
CPC ............... A61B 17/282; A61B 17/30; A61B 2017/2945; A61B 2017/305; A61F 2002/4622; A61F 2/1664
USPC ......................... 606/205, 206, 207, 208, 209
See application file for complete search history.

(56) References Cited

U.S. PATENT DOCUMENTS

| | | |
|---|---|---|
| 1,433,340 A | 10/1922 | Clark |
| 1,561,116 A | 11/1925 | Silliman |
| 2,555,076 A | 5/1951 | Crossley |
| (Continued) | | |

FOREIGN PATENT DOCUMENTS

| | | |
|---|---|---|
| CH | 554239 A | 9/1974 |
| EP | 0010693 A1 | 5/1980 |
| (Continued) | | |

OTHER PUBLICATIONS

International Search Report for International Application No. PCT/US2012/021540, dated Jun. 15, 2012 and dated Jun. 28, 2012.
(Continued)

*Primary Examiner* — Martin T Ton
(74) *Attorney, Agent, or Firm* — Morgan, Lewis & Bockius LLP

(57) ABSTRACT

Surgical introducers aid surgeons in the implantation of medical devices. The introducer provides support and an even distribution of force for ease of insertion and prevention of damage to the medical device while protecting the tissue into which the device is implanted. A representative embodiment includes or consists of a locking device, a pair of forceps, a specially configured and/or angled head with a seat for the device to be implanted, and a gripping area.

25 Claims, 7 Drawing Sheets

(56) References Cited

U.S. PATENT DOCUMENTS

| | | | |
|---|---|---|---|
| 4,036,230 A | 7/1977 | Adams | |
| 4,375,218 A | 3/1983 | DiGeronimo | |
| 4,702,244 A * | 10/1987 | Mazzocco | 606/107 |
| 4,705,035 A | 11/1987 | Givens | |
| 4,739,761 A | 4/1988 | Grandon | |
| 4,844,065 A * | 7/1989 | Faulkner | A61F 2/1664 |
| | | | 606/107 |
| 4,917,677 A | 4/1990 | McCarthy | |
| 5,007,913 A * | 4/1991 | Dulebohn et al. | 606/107 |
| 5,021,057 A | 6/1991 | Byrne, Jr. | |
| 5,387,196 A * | 2/1995 | Green | A61B 17/34 |
| | | | 128/908 |
| 5,484,447 A * | 1/1996 | Waldock et al. | 606/107 |
| 5,797,954 A | 8/1998 | Shaffer et al. | |
| 5,893,853 A | 4/1999 | Arnold | |
| 6,171,324 B1 | 1/2001 | Cote et al. | |
| 6,248,123 B1 * | 6/2001 | McDonald | A61B 17/30 |
| | | | 606/107 |
| 6,251,090 B1 * | 6/2001 | Avery | A61F 9/0017 |
| | | | 604/294 |
| 6,280,449 B1 | 8/2001 | Blake | |
| 6,447,528 B2 | 9/2002 | Paraschac | |
| 6,554,829 B2 * | 4/2003 | Schulze et al. | 606/51 |
| 6,708,587 B1 * | 3/2004 | Noniewicz | B25B 5/06 |
| | | | 81/313 |
| 6,786,926 B2 | 9/2004 | Peyman | |
| 7,160,297 B2 * | 1/2007 | Nesbitt | A47J 36/025 |
| | | | 427/180 |
| 7,972,348 B1 | 7/2011 | Anderson | |
| 2002/0133168 A1 | 9/2002 | Smedley et al. | |
| 2003/0072678 A1 * | 4/2003 | Peterson | A61B 17/30 |
| | | | 422/400 |
| 2003/0233119 A1 * | 12/2003 | Tiedemann | A61B 17/062 |
| | | | 606/210 |
| 2005/0125013 A1 | 6/2005 | Kessler | |
| 2006/0149194 A1 * | 7/2006 | Conston | A61B 17/32002 |
| | | | 604/294 |
| 2006/0258994 A1 | 11/2006 | Avery | |
| 2007/0219582 A1 * | 9/2007 | Brunelle | A61F 2/0805 |
| | | | 606/207 |
| 2007/0233152 A1 * | 10/2007 | Stad et al. | 606/99 |
| 2008/0081952 A1 | 4/2008 | Josephberg | |
| 2008/0200923 A1 * | 8/2008 | Beckman | A61F 9/00781 |
| | | | 606/108 |
| 2008/0255578 A1 | 10/2008 | Neusidl | |
| 2010/0057094 A1 | 3/2010 | Akahoshi | |
| 2010/0106202 A1 | 4/2010 | Gannoe et al. | |
| 2010/0137780 A1 | 6/2010 | Singh et al. | |
| 2010/0331770 A1 * | 12/2010 | Lee | A61K 9/0034 |
| | | | 604/57 |
| 2011/0112546 A1 | 5/2011 | Juan, Jr. et al. | |

FOREIGN PATENT DOCUMENTS

| | | |
|---|---|---|
| FR | 2906997 A1 | 4/2008 |
| FR | 2912901 A1 | 8/2008 |
| NL | 1005694 C2 | 10/1998 |
| WO | 1996/036377 A1 | 11/1996 |
| WO | 1999/030656 A1 | 6/1999 |
| WO | 2001/087200 A1 | 11/2001 |
| WO | WO-08/085966 | 7/2008 |
| WO | 2010/003169 A1 | 1/2010 |

OTHER PUBLICATIONS

International Application No. PCT/US2012/058944, International Search Report dated Apr. 9, 2013, 4 pages.

PCT International Application No. PCT/US2012/058944, International Preliminary Report on Patentability dated Apr. 17, 2014, 8 pages.

* cited by examiner

SURGICAL IMPLANTATION INSTRUMENT

RELATED APPLICATION

This application claims priority to and the benefits of U.S. Ser. No. 61/433,832, filed on Jan. 18, 2011, the entire disclosure of which is hereby incorporated by reference.

BACKGROUND OF THE INVENTION

Medical treatment often requires the administration of a therapeutic agent (e.g., medicament, drugs, etc.) to a particular part of a patient's body. As patients live longer and are diagnosed with chronic and/or debilitating ailments, the likely result will be an increased need to place even more protein therapeutics, small-molecule drugs, and other medications into targeted areas throughout the patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted (and generally offer limited ability to change the dose in response to the clinical picture).

Another example is cancer, such as breast cancer or meningiomas, where large doses of highly toxic chemotherapies, such as rapamycin, bevacizumab (e.g., Avastin), or irinotecan (CPT-11), are typically administered to the patient intravenously, which may result in numerous undesired side effects outside the targeted area. Other examples of difficult-to-reach anatomical regions for drug delivery include the knee, where drugs often have difficulty penetrating the avascular cartilage tissue for diseases such as osteoarthritis, the brain, and the spine.

Implantable drug delivery systems may include a refillable drug reservoir, a cannula for delivering the drug, etc., and generally allow for controlled delivery of pharmaceutical solutions to a specified target. This approach can minimize the surgical incision needed for implantation and typically avoids future or repeated invasive surgery or procedures. In a typical procedure, the pump is implanted using an instrument specifically adapted for the purpose.

Instruments ("introducers") for surgically implanting medical devices tend to have limited capabilities, however. Many implants are difficult to maneuver due to the typically smooth design necessary for implantation in the body, and some devices currently used in surgery can cause damage to the delicate external components of the implant. Surgery may be postponed if the device is damaged by the instrument or slips outside the sterile field due to lack of grip on the device. Medical devices that are inserted into the body are often saturated in sterile water before implantation, further complicating the ability to grip an already smooth (and possibly rounded or even spherical) implant. Many implants also have parylene coatings on the outside, and this layer can also be damaged by contact with the introducer. Finally, polymeric introducers may be subject to buildup of electrostatic charge, which can damage an electronic implantable device.

SUMMARY OF THE INVENTION

Embodiments of the present invention aid surgeons in the implantation of medical devices. The introducer provides support and an even distribution of force for ease of insertion and prevention of damage to the medical device while protecting the tissue into which the device is implanted. While the introducer can be used for many types of implants (e.g., drug pumps, pacemakers, or other neural stimulators), embodiments of the invention can be particularly helpful in the insertion of implants that are delicate in nature (e.g., microelectronic devices or infusion pumps with flexible cannulas) or very small devices that are difficult to manipulate with hands or surgical tweezers (e.g., implantable peripherhal nerve stimulators or intraocular drug pumps).

A representative embodiment of the invention includes or consists of a locking device, a pair of forceps, a specially configured and/or angled head with a seat for the device to be implanted, and a gripping area. The device may also include application-specific markings to aid the surgeon in measurement and an illumination source. The head members, when united around an implantable device, may be shaped to follow the contours of the device and to slide easily between small spaces (e.g., the subconjunctival space) without causing damage to delicate tissue.

Accordingly, in a first aspect, the invention relates to a tool or instrument facilitating surgical implantation of an implantable device. In various embodiments, the instrument comprises first and second of forceps arms each having first and second ends; the arms are joined at the first ends thereof and are arranged to oppose but permit resisted compression of the arms toward each other. A first-arm head member is located at the second end of the first arm and a second-arm head is member located at the second end of the second arm. The head members are angled away from each other relative to an axis running between and coplanar with the arms, and are shaped to releasably engage the implantable device upon compression of the arms.

The instrument may further comprise a releasable catch for maintaining the arms in a compressed configuration; for example, the catch may be operable by a thumb-engageable slide disposed on the first arm. In some embodiments, the slide is slidable along an angled path relative to the first arm. In other embodiments, instead of a releasable catch, the instrument comprises a finger-operable rotation member affixed to a leadscrew along an axial length thereof; the leadscrew passes through threaded openings in the first and second arms such that rotation of the rotation member alters a distance between the arms. The finger-operable rotation member may be disposed between the arms.

In some embodiments, the instrument comprises depth markings along the first arm indicating a distance from a terminus of the heads. The second-arm head may have an angled curvature that is complementary to an internal anatomical contour, e.g., an ocular orbit. The head members have opposed surfaces for releasably engaging the implantable device upon compression of the arms, and these surfaces may have a texture and/or a polymeric coating providing stiction with the implantable devices to discourage movement thereof. In some embodiments, at least the head members are coated with a biocompatible polymer (e.g., parylene). The biocompatible polymer may, in some cases, be infused with a drug.

Some embodiments also feature means for reducing or preventing damage due to the buildup of electrostatic charge on the instrument; electrostatic discharge (ESD) can damage or destroy delicate electronic circuitry. In one embodiment, the introducer is made from or coated with an electrically dissipative material, e.g., a conductive polymer or a polymer loaded with a conductive pigment, such as carbon black; a suitable commercial example is the TECAFORM SD material. Although such a material is not highly conductive, charge cannot build up on its surface. Because the clinician will typically be grounded, an ESD-safe introducer is desirably retained on a grounded (e.g., through a conductive (0Ω) or dissipative (e.g., 1 MΩ) instrument tray when not in use. Alternatively, a conductive wire may connect the introducer to ground.

In another aspect, an instrument according to the invention comprises, in various embodiments, first and second of forceps arms each having first and second ends, the arms being pivotable at the first ends thereof; a first-arm head member located at the second end of the first arm; a second-arm head member located at the second end of the second arm; and a finger-operable rotation member affixed to a leadscrew along an axial length thereof. The leadscrew passes through threaded openings in the first and second arms such that rotation of the rotation member alters a distance between the arms. The head members are angled away from each other relative to an axis running between and coplanar with the arms, and are shaped to releasably engage the implantable device upon compression of the arms. The rotation member may be aligned with the axis.

In still another aspect, the invention pertains to a combination comprising an implantable device and, retained therein, a instrument facilitating its surgical implantation. In various embodiments, the combination comprises first and second forceps arms each having first and second ends, the arms being joined at the first ends thereof and arranged to oppose but permit resisted compression of the arms toward each other; a first-arm head member located at the second end of the first arm; a second-arm head member located at the second end of the second arm; and an implantable medical device. The head members are angled away from each other relative to an axis running between and coplanar with the arms, and releasably engage the implantable device.

The terms "substantially" and "approximately" mean±10% (e.g., by weight or by volume), and in some embodiments, ±5%.

DESCRIPTION OF DRAWINGS

The foregoing will be more readily understood from the following detailed description, in particular, when taken in conjunction with the drawings, in which.

DETAILED DESCRIPTION

Figure 1:
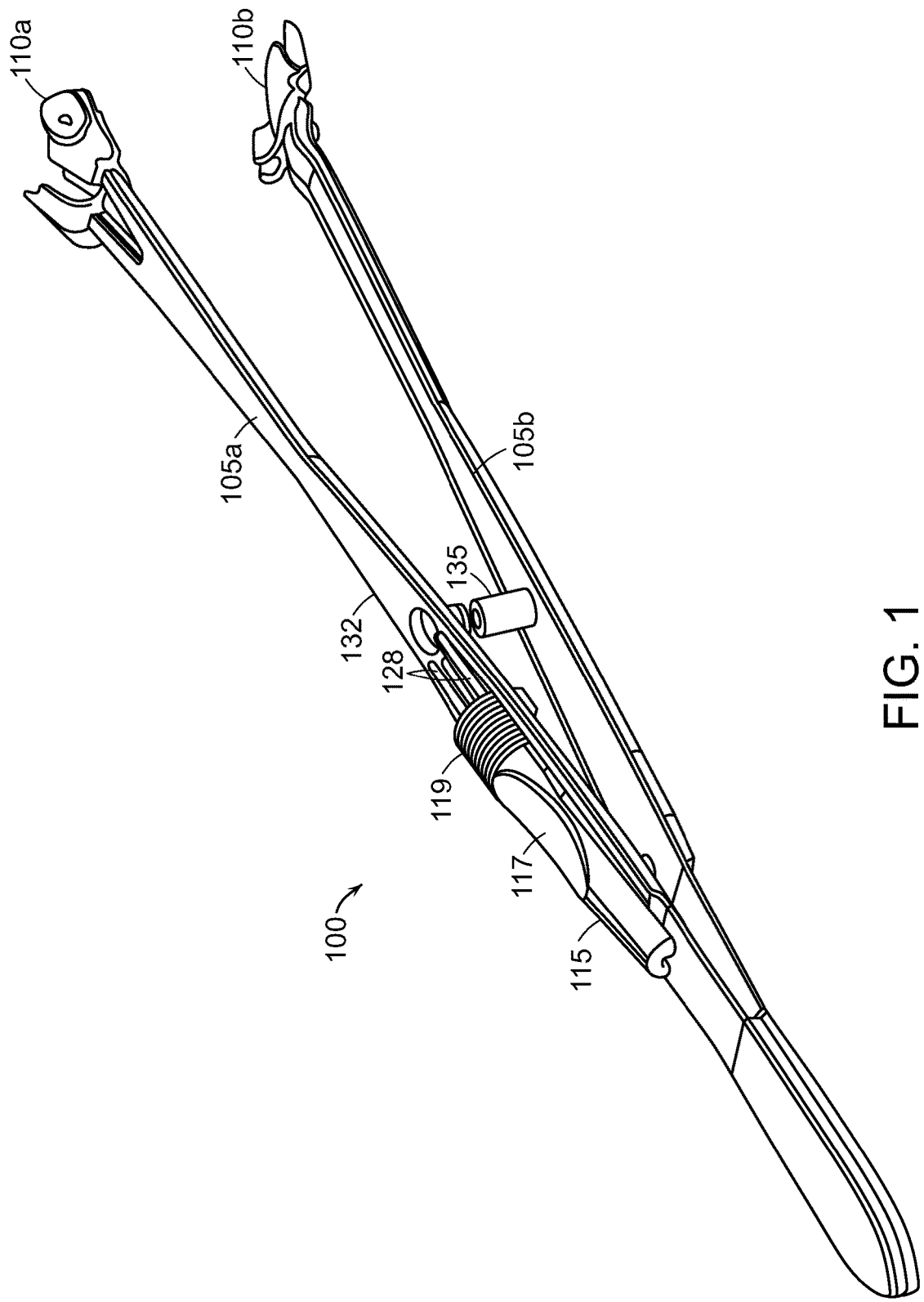
FIG. 1 is a perspective view of an introducer in accordance with an embodiment of the present invention.

Refer first to FIG. 1, which illustrates an introducer 100 in accordance with an embodiment of the invention. The introducer 100 includes two forceps arms 105a, 105b joined at one end thereof. The arms may be made of a metal (such as steel or titanium) or a disposable plastic (such as polyethylene or polystyrene), and are angled away from the joined ends so that they naturally assume an open position and, due to the joined ends, yieldingly resist compression in the manner of tweezers—i.e., the arms 105a, 105b exhibit a preloaded amount of resilient force that permits controlled compression by the user without excessive effort, but also with sufficient resistance to avoid unintended collapse. In some embodiments, this resilient force is provided or enhanced by a spring (not shown) between the arms 105a, 105b.

Figure 2:
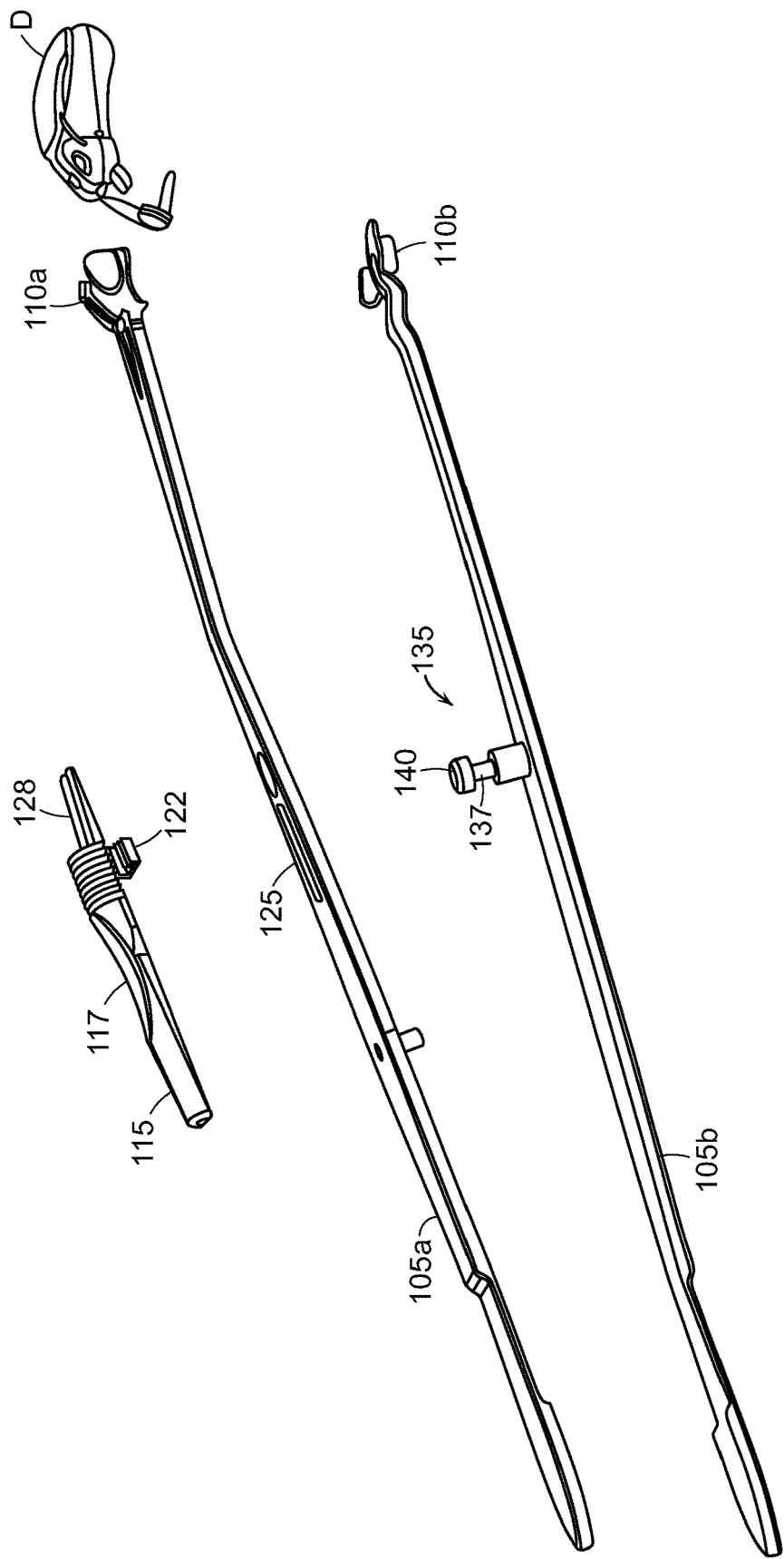
FIG. 2 is an exploded view of the embodiment shown in FIG. 1.

The unjoined ends of the arms 105a, 105b terminate in complementary head members 110a, 110b. These head members 110 typically flare outwardly and are configured to engage the device to be implanted, as described below. The introducer 100 may include a locking mechanism that retains the arms 105a, 105b in the compressed configuration. With reference to FIGS. 1 and 2, the locking mechanism may be a releasable catch operable by means of a thumb-engageable slide 115. The slide 115 includes a depression 117 shaped to receive the user's thumb and is slidably mounted for travel along, and parallel to, arm 105a. The forward end 119 of the slide may be knurled or ribbed for further engagement with the user's thumb. As shown in FIG. 2, slide mounting may achieved using an inverted T member 122 depending from the underside of the slide 115, and which engages a slot 125 in arm 105a. The shank of T member 122 extending from slide 115 travels within slot 125, and the crosspiece of the T member travels along the underside of arm 105a and prevents disengagement of slide 115 therefrom. Extending from the forward end 119 of the slide 115 are a pair of rails 128. As slide 115 travels forward, rails 128 pass over an aperture 130 through arm 105a. A post 135 is mounted on, and projects upwardly from, arm 105b below aperture 130. The post 135 includes a narrow (smaller-diameter) neck segment 137 and a wider cap or flange 140 thereabove. When the arms 105a, 105b are compressed, a portion of post 135 including the neck 137 and cap 140 passes through the aperture 132 through arm 105a. The rails 122 are spaced apart by a distance greater than the diameter of neck segment 137 of post 135 but less than the diameter of the cap 140, so that the rails slide along the neck segment 137 and engage the underside of cap 140 when the arms 105a, 105b are released.

Figure 3:
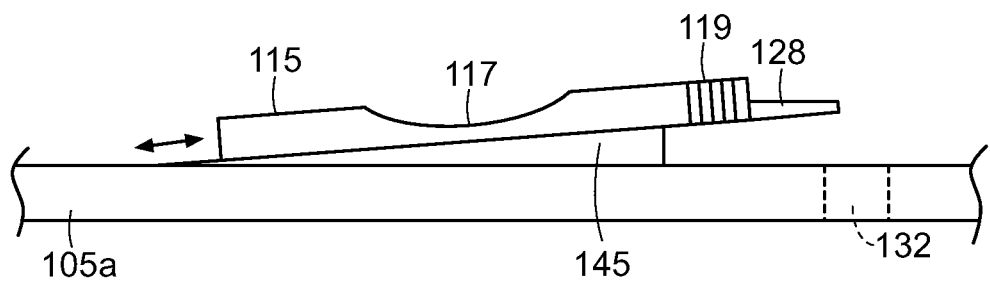
FIG. 3 is a close-up elevation showing an angled travel path for the thumb-engageable slide shown in FIG. 2.

As shown in FIG. 3, the slide 115 can, if desired, be configured for slow release by traveling at an angle to arm 105a rather than directly parallel thereto—for example, along a wedge 145 mounted on arm 105a. In this way, the rails 122 rise relative to the flat surface of arm 105 as the slide 115 is pushed forward, thereby squeezing the arms 105a, 105b together as the rails engage the post 135; as the slide 115 is retracted, the arms are allowed to gradually open. Expansion of the arms is thereby limited by the position and travel of slide 115, even if the user suddenly releases the arms.

Figure 4:
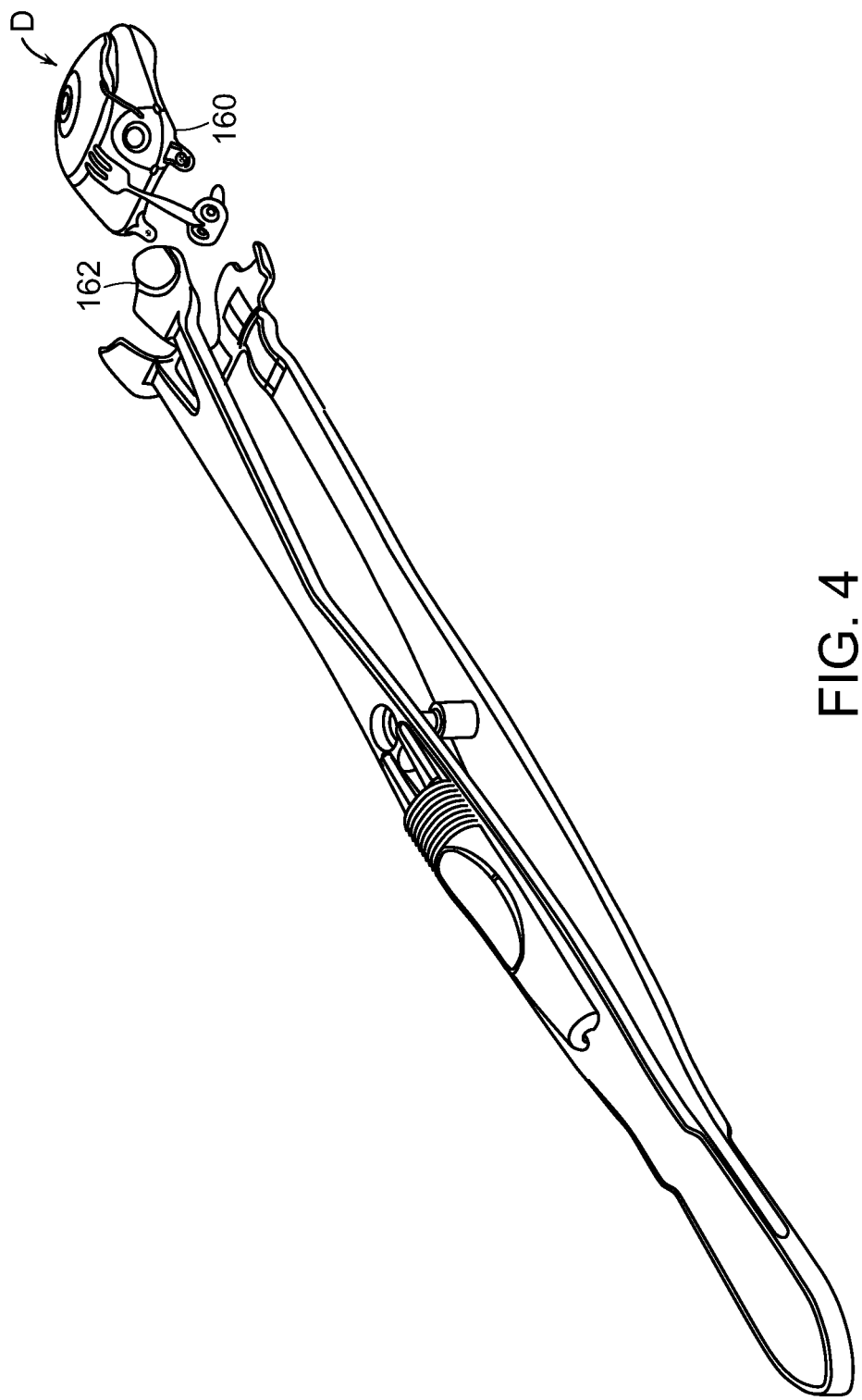
FIG. 4 is another perspective view of the introducer shown in FIG. 1, here in a partially closed position.

As shown in FIGS. 4 and 5, the head members 110a, 110b have shapes complementary to the implantable device D that the instrument will handle. For example, the device may be an implantable drug pump as described, e.g., in U.S. Patent Publ. No. 2006/0258994, entitled "Implantable delivery device for administering pharmacological agents to an internal portion of a body," the entire disclosure of which is hereby incorporated by reference. Ideally there will be one or more convex elements along the contour of the device D—such as the refill port 160—that mates with a complementary recession 162 in one of the head members 110, thereby preventing the device D from slipping out of the instrument 100 without excessive clamping force being applied to the device D. As further described below, the instrument 100 may include features that restrict the closure of arms 105, thereby limiting the clamping force. When united, the head members 110 should slide easily between small spaces (e.g., the subconjunctival space) without causing damage to delicate tissue. Furthermore, head members 110a, 110b can be fashioned in different configurations, e.g., formatted to allow opening and closing in a longitudinal or axial orientation to improve ease of use. Optionally, markings at specific distances (e.g., in millimeter increments indicative of the distance to the distal edge of the heads 110) can be applied to one or both of the arms 110 to guide the surgeon in determining when the device D has reached its optimum or required depth. With a slight movement of the thumb, the surgeon may readily release the locking mechanism as described above, allowing the introduced device D to stay in place while the introducer 100 is removed.

The head members 110a, 110b may have textured or tacky interior surfaces (i.e., the surfaces that make contact with the device D). Most simply, a suitable polymeric coating such as silicone may be applied to the head members 110a, 110b (or just the interior surfaces thereof) and cured (or merely allowed to dry) to form a coating with the desired stiction to discourage movement of the device D. Alternatively, the heads 110 and, indeed, the entire introducer 100 can be coated with a biocompatible material (e.g., parylene) for an optimized smooth interface, since many implants are difficult to maneuver due to the typical smooth design necessary for implantation. Further, these coatings may be infused with application-specific drugs (e.g. anti-inflammatory, anti-infective drugs). A coating may be applied to the head 110 and/or the arms 105 by dip coating, spray coating, manual painting, or any other suitable application technique.

Once the medical device is in place, the introducer can easily be released and removed (either before or after suturing). The introducer may provide means for the surgeon to precisely place sutures in optimal places along the implant. Furthermore, the introducer may be angled as necessary to accommodate the implant and the surgeon's needs simultaneously. For example, in the case of an implantable drug pump, the introducer may be configured to hold the pump in aseptic conditions, facilitating filling in the operating room and allowing the surgeon to hold the pump steady during the initial fill process. Moreover, the instrument may be prepackaged with the implant, which allows the operator to fill the device in the operating room. A dilator may be used in combination with the introducer.

Figure 5A:
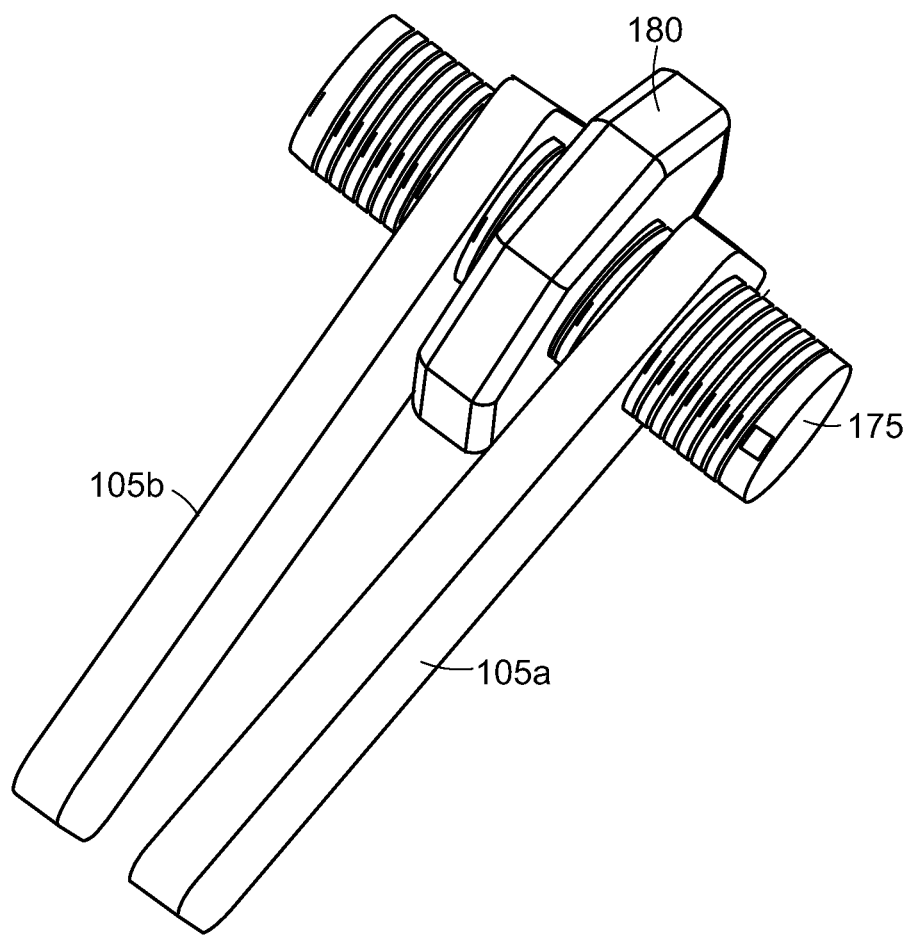
FIGS. 5A and 5B illustrate a gear wheel with a threaded rod for precisely opening or compressing the forceps arms.
Figure 5B:
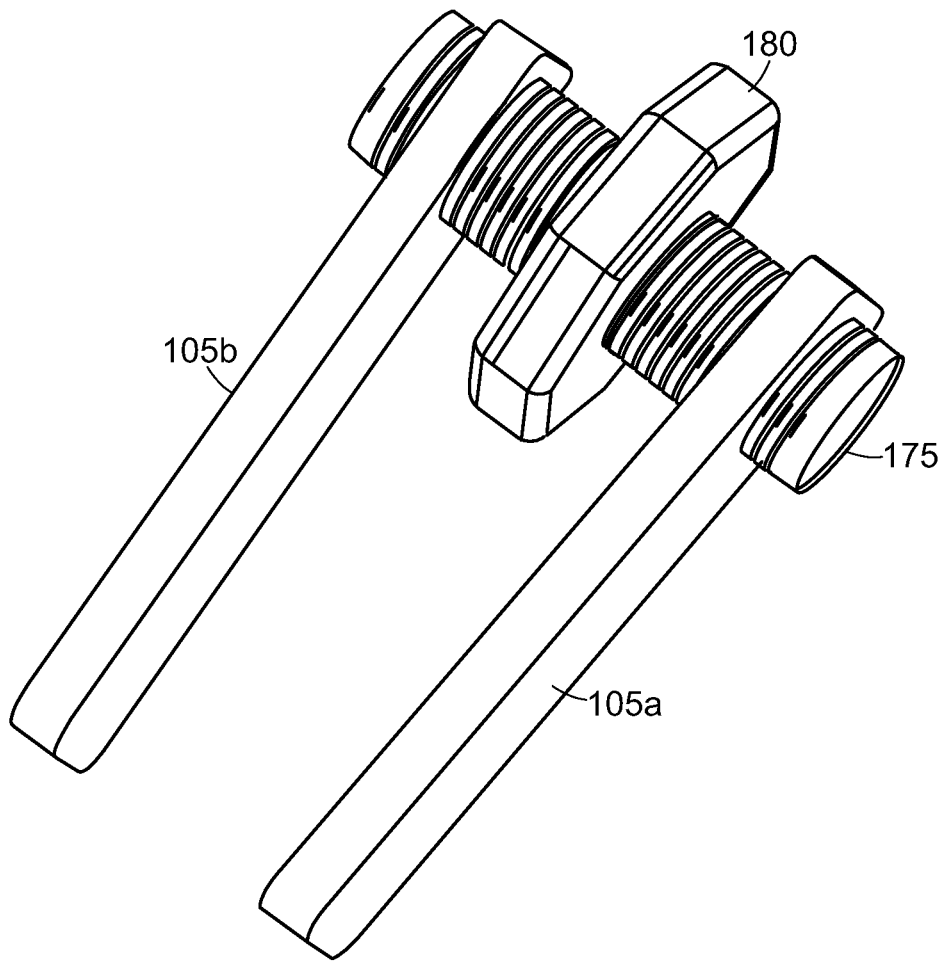
Figure 6:
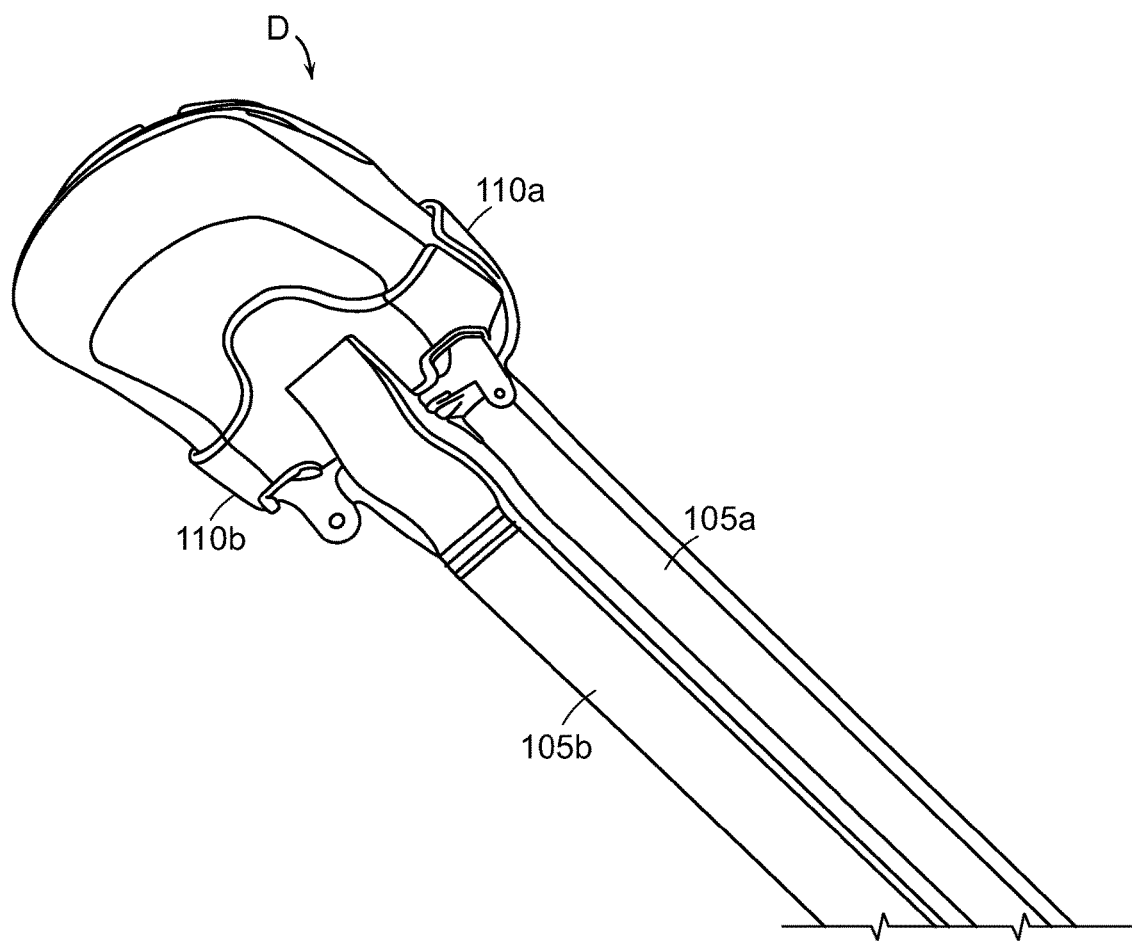
FIG. 6 is a close-up view from the bottom showing an implantable device grasped by the introducer.

As described above, the introducer 100 may operate by compression and release, or may have a restriction mechanism—such as an angled travel path for the slide—that allows movement of the slide rather than squeezing or release of the arms to dictate the rate of compression or release. To provide further precision in controlling the spread of arms 105a, 105b, the locking mechanism described above may be replaced with a finger-operated leadscrew 175, as illustrated in FIGS. 5A, 5B. Located, for example, where post 135 would otherwise be placed, the leadscrew 175 threadably engages opposed bores through the arms 105a, 105b. A thumbwheel, gear or polygonal nut 180 allows the user to rotate the leadscrew 175 with her thumb or other finger, thereby expanding or reducing the distance between the arms 105a, 105b depending on the direction and extent of rotation. The threading pitch can be selected to facilitate a desired rate of opening and closing (relative to rotation of the leadscrew), and the threading on the leadscrew 175 can terminate at desired locations proximal and distal to the thumbwheel 180 in order to limit the degree of allowed closing and opening of the arms 105a, 105b, preventing damage to the implant and tissue surrounding the implant, respectively. With this mechanism, the arms 105 need not be joined in a manner that produces resistance to compression; the arms 105 may, instead, simply be hinged. As shown in FIG. 6, the head members 110a, 110b should unite snugly around the device D but must not apply a damaging force thereto. Other mechanisms to control the opening and closing of the arms 105 include a button, clip, or other comparable mechanism.

Good manufacturing procedures, particularly those relating to the head members 110, are critical. The head members must precisely conform to the medical device they are designed for and avoid damage to surrounding tissue during implantation. Accordingly, burrs or sharp edges should be minimized or eliminated during the manufacturing process. In one representative procedure, a flat piece is stamped out of a thin sheet of stainless steel. Next, a series of tools is used to shape the head members 110 in an incremental fashion, and if desired, the head members are coated as described above.

Although the present invention has been described with reference to specific details, it is not intended that such details should be regarded as limitations upon the scope of the invention, except as and to the extent that they are included in the accompanying claims.

What is claimed is:

1. An instrument facilitating surgical implantation of an implantable device having two opposed surface portions at least one of which has a curved surface contour, the instrument comprising:
    first and second forceps arms each having first and second ends, the arms being joined at the first ends thereof and arranged to oppose but permit resisted compression of the arms toward each other into a closed position from an open position, wherein compression of the arms toward each other into the closed position forces the second ends of the arms toward each other;
    a first-arm head member, having a first length defined by a distal end and a proximal end thereof, located at the second end of the first arm; and
    a second-arm head member, having a second length defined by a distal end and a proximal end thereof, located at the second end of the second arm,
    wherein:
    (i) the head members are flared outwardly so as to be angled away from each other along the entire first and second lengths thereof at least in the open position relative to an axis running between and coplanar with the arms,
    (ii) each of the head members defines an interior surface, the interior surfaces being opposed to each other and differently shaped to releasably engage the implantable device without damage thereto upon compression of the arms into the closed position,
    (iii) the interior surface of at least one of the head members has a curved portion complementary to the curved surface contour of the implantable device whereby closure of the arms causes the head members to opposedly engage the surface contour of the implantable device to prevent release thereof from the instrument in the closed position, and
    (iv) the differently shaped interior surfaces mate with different surface contours of the implantable device.

2. The instrument of claim 1 further comprising a releasable catch for maintaining the arms in a compressed configuration, the catch being operable by a thumb-engageable slide disposed on the first arm.

3. The instrument of claim 2 wherein the slide is slidable along an angled path relative to the first arm.

4. The instrument of claim 1 further comprising a finger-operable rotation member affixed to a leadscrew along an axial length thereof, the leadscrew passing through threaded openings in the first and second arms such that rotation of the rotation member alters a distance between the arms.

5. The instrument of claim 4 wherein the finger-operable rotation member is disposed between the arms.

6. The instrument of claim 1 further comprising depth markings along the first arm indicating a distance from a terminus of the heads.

7. The instrument of claim 1 wherein the second-arm head has an angled curvature that is complementary to an internal anatomical contour.

8. The instrument of claim 7 wherein the internal anatomical contour is an ocular orbit.

9. The instrument of claim 1 wherein the head members have opposed surfaces for releasably engaging the implantable device upon compression of the arms, the opposed head-member surfaces having a texture.

10. The instrument of claim 1 wherein the head members have opposed surfaces for releasably engaging the implantable device upon compression of the arms, the opposed head-member surfaces having a contour complementary to the contour of the implantable device.

11. The instrument of claim 1 wherein the head members have opposed surfaces for releasably engaging the implantable device upon compression of the arms, the opposed head-member surfaces having a polymeric coating providing stiction with the implantable devices to discourage movement thereof.

12. The instrument of claim 11 wherein the biocompatible polymer is infused with a drug.

13. The instrument of claim 11 wherein the biocompatible polymer is parylene.

14. The instrument of claim 1 wherein at least the head members are coated with a biocompatible polymer.

15. The instrument of claim 1 further comprising means for reducing electrostatic charge on the instrument during use thereof.

16. The instrument of claim 15, wherein the means for reducing electrostatic charge comprises an electrically dissipative material defining or coating at least a portion of the instrument for preventing buildup of electrostatic charge on the instrument during use.

17. The instrument of claim 15, wherein the means for reducing electrostatic charge comprises a conductive wire connecting the instrument to ground during use.

18. The instrument of claim 1, wherein the head members have an exterior shape following contours of the implantable device upon engagement thereof and are thereby easily slidable between small spaces without causing damage to delicate tissue.

19. The instrument of claim 1, wherein the interior surface of the head members comprises a recession complementary in shape to a convex element along a surface contour of the implantable device, whereby the recession mates to the convex element to further prevent release of the implantable device.

20. The instrument of claim 1, wherein one of the head members is forked.

21. The instrument of claim 1, wherein the curved portion of the interior surface contacts the complementary surface portion of the implantable device upon engagement of the head members with the implantable device.

22. A combination comprising an implantable drug pump and an instrument retaining the implantable drug pump and facilitating its surgical implantation, the combination comprising:
first and second forceps arms each having first and second ends, the arms being joined at the first ends thereof and arranged to oppose but permit resisted compression of the arms toward each other into a closed position from an open position, wherein compression of the arms toward each other into the closed position forces the second ends of the arms toward each other;
a first-arm head member, having a first length defined by a distal end and a proximal end thereof, located at the second end of the first arm;
a second-arm head member, having a second length defined by a distal end and a proximal end thereof, located at the second end of the second arm; and
an implantable drug pump having two opposed surface portions at least one of which has a curved surface contour,
wherein the head members are flared outwardly so as to be angled away from each other along the entire first and second lengths thereof at least in the open position relative to an axis running between and coplanar with the arms, each defining an interior surface, the interior surfaces being opposed to each other and differently shaped for oppositely and releasably engaging the implantable drug pump without damage thereto upon compression of the arms into the closed position, at least one of the interior surfaces having a curved portion complementary to the curved surface contour of the implantable drug pump, the differently shaped interior surfaces mating with different surface contours of the implantable device.

23. The combination of claim 22, wherein:
the implantable drug pump comprises a convex element along the curved surface contour; and
the curved portion of the at least one of the interior surfaces comprises a recession complementary in shape to the convex element, whereby the recession mates to the convex element to further prevent release of the implantable drug pump.

24. The combination of claim 23, wherein the convex element comprises a refill port.

25. The combination of claim 22, wherein, upon engagement with the implantable drug pump, the head members each (i) cover only a part of the surface portion of the implantable drug pump engaged thereto, thereby leaving an uncovered part of the surface portion, and (ii) have an external surface contour following the uncovered part of the surface portion of the implantable drug pump engaged thereto, whereby the engaged implantable drug pump is easily slidable between small spaces without causing damage to delicate tissue.

* * * * *